United States Patent
Rock et al.

(10) Patent No.: US 8,696,717 B2
(45) Date of Patent: Apr. 15, 2014

(54) MULTI-PLANAR, TAPER LOCK SCREW WITH ADDITIONAL LOCK

(75) Inventors: Andrew T. Rock, Spring Grove, PA (US); Michael Barrus, Ashburn, VA (US); Scott Jones, McMurray, PA (US); Kevin R. Strauss, Leesburg, VA (US)

(73) Assignee: K2M, Inc., Leesburg, VA (US)

( * ) Notice: Subject to any disclaimer, the term of this patent is extended or adjusted under 35 U.S.C. 154(b) by 701 days.

(21) Appl. No.: 12/612,843

(22) Filed: Nov. 5, 2009

(65) Prior Publication Data
US 2010/0114180 A1  May 6, 2010

Related U.S. Application Data

(60) Provisional application No. 61/198,380, filed on Nov. 5, 2008.

(51) Int. Cl.
*A61B 17/86* (2006.01)
*A61B 17/70* (2006.01)

(52) U.S. Cl.
USPC ........... 606/308; 606/305; 606/306; 606/266; 606/267; 606/328

(58) Field of Classification Search
USPC .................. 606/266–271, 305–308, 319, 328
See application file for complete search history.

(56) References Cited

U.S. PATENT DOCUMENTS

| | | |
|---|---|---|
| 4,950,269 A | 8/1990 | Gaines, Jr. |
| 5,683,392 A | 11/1997 | Richelsoph et al. |
| 5,738,685 A | 4/1998 | Halm et al. |
| 5,885,286 A | 3/1999 | Sherman et al. |
| 6,010,503 A | 1/2000 | Richelsoph et al. |
| 6,074,391 A | 6/2000 | Metz-Stavenhagen et al. |
| 6,110,172 A | 8/2000 | Jackson |
| 6,132,434 A | 10/2000 | Sherman et al. |
| 6,254,602 B1 | 7/2001 | Justis |
| 6,273,888 B1 | 8/2001 | Justis |
| 6,296,642 B1 | 10/2001 | Morrison et al. |
| 6,302,888 B1 | 10/2001 | Mellinger et al. |
| 6,413,258 B1 | 7/2002 | Bernhardt, Jr. |
| 6,440,132 B1 * | 8/2002 | Jackson ...................... 606/308 |
| 6,827,719 B2 | 12/2004 | Ralph et al. |
| 6,835,196 B2 | 12/2004 | Biedermann et al. |
| 6,837,889 B2 | 1/2005 | Shluzas |
| 6,843,791 B2 | 1/2005 | Serhan |
| 6,869,433 B2 | 3/2005 | Glascott |
| 6,884,244 B1 | 4/2005 | Jackson |
| 6,893,443 B2 | 5/2005 | Frigg et al. |
| 6,896,677 B1 | 5/2005 | Lin |
| 6,918,911 B2 | 7/2005 | Biedermann et al. |
| 6,945,975 B2 | 9/2005 | Dalton |
| 7,090,674 B2 | 8/2006 | Doubler et al. |

(Continued)

*Primary Examiner* — Eduardo C. Robert
*Assistant Examiner* — Julianna N Harvey
(74) *Attorney, Agent, or Firm* — Carter, DeLuca, Farrell & Schmidt, LLP

(57) ABSTRACT

A pedicle screw construct includes a pedicle screw, a coupling, a collet, and a set screw. The pedicle screw includes a shank having a helical thread formed thereon and a head at one end. The collet is positioned atop the head of the pedicle screw. The collet and pedicle screw are inserted into the coupling. The set screw is positioned in the collet such that the set screw contacts a portion of the rod and is releasably secured to the pedicle screw via a gripping tool. The pedicle screw is rotatable and pivotable relative to the collet and coupling assembly.

16 Claims, 9 Drawing Sheets

(56) References Cited

U.S. PATENT DOCUMENTS

| | | |
|---|---|---|
| 7,105,029 B2 | 9/2006 | Doubler et al. |
| 7,118,303 B2 | 10/2006 | Doubler et al. |
| 7,334,961 B2 | 2/2008 | Doubler et al. |
| 7,335,201 B2 | 2/2008 | Doubler et al. |
| 7,445,627 B2 | 11/2008 | Hawkes et al. |
| 7,658,582 B2 | 2/2010 | Doubler et al. |
| 7,678,136 B2 | 3/2010 | Doubler et al. |
| 2002/0143341 A1* | 10/2002 | Biedermann et al. ........... 606/73 |
| 2005/0053423 A1 | 3/2005 | Doubler et al. |
| 2005/0080415 A1* | 4/2005 | Keyer et al. ..................... 606/61 |
| 2006/0173456 A1 | 8/2006 | Hawkes et al. |
| 2006/0200128 A1* | 9/2006 | Mueller .......................... 606/61 |
| 2006/0271047 A1 | 11/2006 | Jackson |
| 2006/0276792 A1 | 12/2006 | Ensign et al. |
| 2007/0093817 A1 | 4/2007 | Barrus et al. |
| 2007/0286703 A1 | 12/2007 | Doubler et al. |
| 2008/0137933 A1 | 6/2008 | Kim |
| 2008/0243193 A1 | 10/2008 | Ensign et al. |

* cited by examiner

MULTI-PLANAR, TAPER LOCK SCREW WITH ADDITIONAL LOCK

CROSS REFERENCE TO RELATED APPLICATIONS

The present application claims priority from U.S. Provisional Patent Application No. 61/198,380 filed Nov. 5, 2008, the contents of which are incorporated herein by reference.

BACKGROUND

1. Technical Field

The present disclosure relates to pedicle screws and, more particularly, to a pedicle screw having a proximal flange that is easily accessible to facilitate the connection of a gripping tool for locking and unlocking the pedicle screw.

2. Background of Related Art

The human spine is the supporting axis of the body and makes all the movement of a person's head, arms, and legs possible. It is a highly flexible structure, capable of a high degree of curvature and twist in nearly every direction. An adult spine generally has twenty-four vertebrae, which may be categorized into three major sections. These categories include the cervical spine, the thoracic spine, and the lumbar spine. The cervical spine is composed of the upper seven vertebrae, the thoracic spine is composed of the next twelve vertebrae, and the lumbar spine is composed of the final five vertebrae. Below the lumbar spine is a bone called the sacrum, which is part of the pelvis. Muscles and ligaments are attached to a slender projection from the back of the vertebrae known as the spinous process. Housed within a narrow channel in the center of spine is the spinal cord. All the nerves of the body are connected to the spinal cord.

Spinal pathologies, whether the result of genetic or developmental irregularities, trauma, chronic stress, tumors, or disease may limit the spine's range of motion or threaten critical elements of the nervous system housed within the spine. A variety of systems to correct the alignment of the spinal vertebrae involving the implantation of artificial assemblies in or on the spine have been devised.

For example, it is a common surgical requirement to stabilize and fix bones and bone fragments in a particular spatial relationship to correct the location of skeletal components due to injury or disease. This may be accomplished by using a number of bone pins, anchors, or screws placed in bones across a discontinuity in the bone or bone fragments, such as a fracture, or adjacent vertebrae, or a joint, connected by a rod to maintain a predetermined spatial location of the bones or bone fragments. In some cases, the use of these devices may be permanently implanted in the subject. In other cases, the devices may be implanted only as a temporary means of stabilizing or fixing the bones or bone fragments, with subsequent removal when no longer needed. It is also common that device implants that were intended to be permanent may require subsequent procedures or revisions as the dynamics of the subject's condition warrant. Additionally, spinal fixation apparatuses are widely employed in surgical processes for correcting spinal injuries and diseases. These apparatuses commonly employ longitudinal link rods secured to the bone such as vertebrae by spinal bone fixation fasteners such as pedicle screws, hooks and others.

Moreover, depending upon how such systems are coupled to the spine, the systems may be classified as anterior, posterior, or lateral implants. For example, lateral and anterior systems are coupled to the anterior portion of the spine. Posterior systems generally comprise a pair of rods that are fixed to adjacent vertebrae with pedicle screws or hooks on either side of the spinous process along a section of the spine. Achieving the optimum alignment of a system with the vertebrae to which it is to be coupled is limited by the range of motion achievable by the system, i.e., the greater the range of motion achievable by the assembly, the more closely aligned the assembly may be with the vertebrae. In addition to the limited range of motion achievable by current systems, currently available systems are often complex, unreliable, and difficult to manipulate.

SUMMARY

A pedicle screw construct includes a coupling having an opening extending therethrough and a collet configured to be receivable in the opening of the coupling. The pedicle screw further includes a head configured to be receivable in an opening of the collet. The pedicle screw also includes a shank, a head having a top and a bottom surface, and a neck between the bottom of the head and the shank, the head configured to be receivable in an opening of the collet such that the pedicle screw is movable throughout a plurality of positions. Additionally, the pedicle screw includes an set screw configured to be receivable in the collet such that the set screw contacts a portion of the rod, where the set screw is releasably secured via a gripping tool.

In an alternate embodiment, a pedicle screw construct is presently disclosed including a coupling having an opening extending therethrough and a collet configured to be releasably secured to an outer portion of the coupling. The collet includes at least two wings for grasping the outer portion of the coupling and a centrally positioned opening. The pedicle screw further includes a head configured to be receivable in an opening of the collet. The pedicle screw also includes a shank, a head having a top and a bottom surface, and a neck between the bottom of the head and the shank, the head configured to be receivable in an opening of the collet such that the pedicle screw is movable throughout a plurality of positions.

The collet may further include a bottom edge having an annular beveled lip extending upwards and inwards from the bottom outer edge of the collet, and the coupling may further include a bottom edge having an annular beveled lip extending upwards and inwards from the bottom outer edge of the coupling.

The shank may further include a helical thread formed thereon. The neck may have a diameter that is less than a diameter of the bottom of the head or a diameter of the helical thread of the shank.

BRIEF DESCRIPTION OF THE DRAWINGS

Embodiments of the presently disclosed pedicle screw construct are described herein with reference to the accompanying drawings, wherein.

DETAILED DESCRIPTION OF THE EMBODIMENTS

Figure 1A:
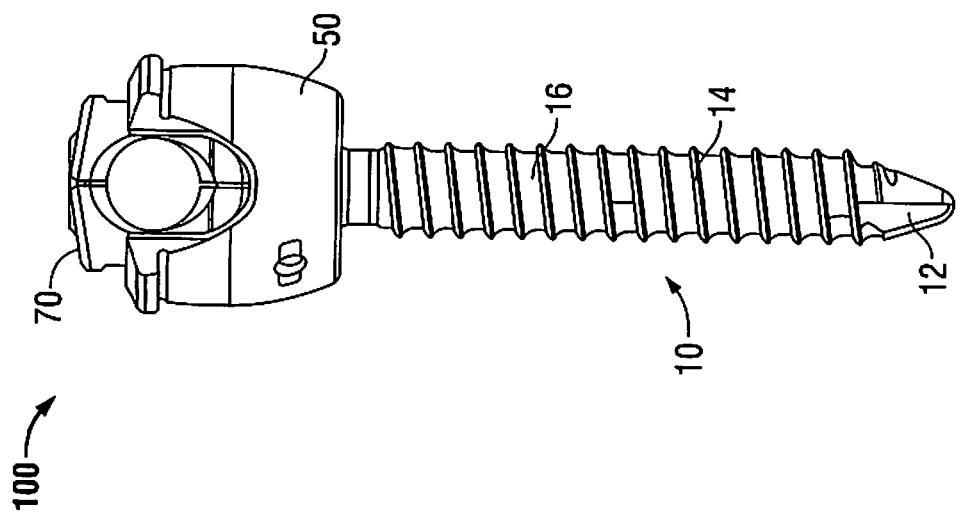
FIG. 1A is a top perspective view of a pedicle screw having a taper lock.
Figure 1B:
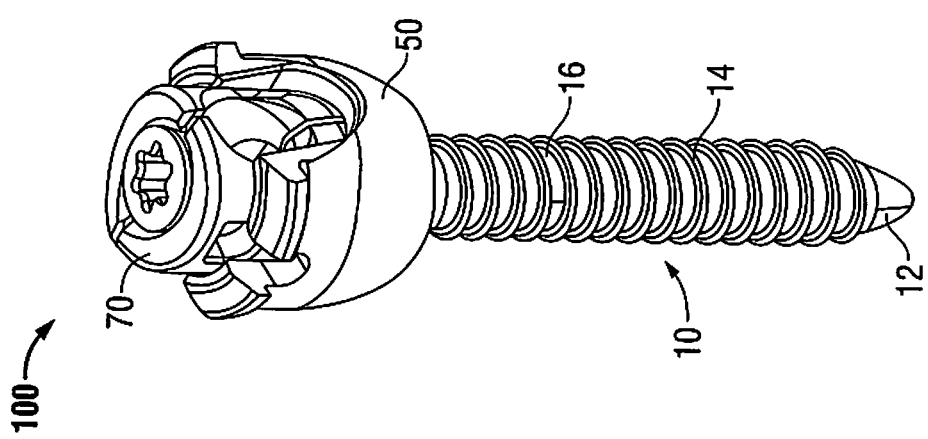
FIG. 1B is a front view of the pedicle screw of FIG. 1A.
Figure 1C:
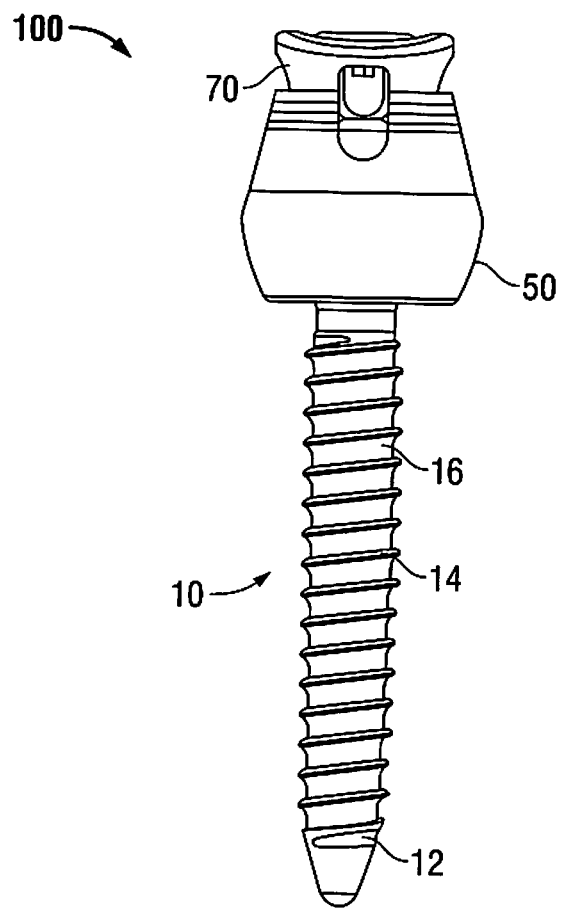
FIG. 1C is a side view of the pedicle screw of FIG. 1A.
Figure 1D:
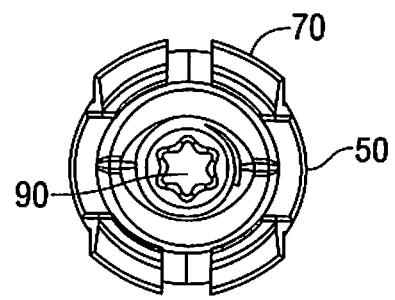
FIG. 1D is a top view of the pedicle screw of FIG. 1A.

Embodiments of the presently disclosed pedicle screw will now be described in detail with reference to the drawing figures wherein like reference numerals identify similar or identical elements. In the drawings and in the description which follows, the term "proximal", as is traditional, will refer to the end of the pedicle screw which is closest to the operator while the term "distal" will refer to the end of the pedicle screw which is farthest from the operator.

The present disclosure generally relates to orthopedic surgery, and in particular to devices for stabilizing and fixing the bones and joints of the body. Particularly, the present disclosure relates to a multi-planar, taper lock screw for securing a spinal rod to a vertebra. The screw may be inserted into a vertebra and connected to a spinal rod that may be connected to other vertebrae not on the same plane. Additionally, the screw may provide a structural configuration that facilitates ease of insertion or removal of the screw as desired.

The present disclosure further relates to a multi-planar, taper lock screw having a proximal flange that is conveniently and easily accessible to facilitate the connection of a gripping tool for improved ease of locking and unlocking of the screw when desired. More specifically, the present disclosure further relates to using a locking cap or set screw to further secure the rod to the screw construct. Thus, the present disclosure relates to a device that may be easily or conveniently locked and/or unlocked (releasably secured), as desired by, for example, a surgeon. The device may be easily grasped by a complementary tool, such as a gripping device, for securedly locking and/or unlocking the rod and screw.

Referring to FIGS. 1A-1F, in which like reference numerals identify similar or identical elements, a pedicle screw construct is generally designated as 100. The pedicle screw construct 100 includes a pedicle screw 10, a pin 30, an outer housing or coupling 50, and an inner housing or collet 70. The pedicle screw 10 includes a shank 16 having a helical thread 14 formed thereon. A cutting portion 12 is formed at a distal end of the pedicle screw 10. A head 18 is located at a proximal end of the pedicle screw 10. A neck 16a (see FIGS. 1B, 1C, 1E) extends between a bottom surface of the head 18 and the beginning of the helical thread 14.

The pedicle screw construct 100 will now be discussed as assembled for use. The collet 70 may be seated atop the head 18 (see FIG. 1E) of pedicle screw 10. The opening at the bottom of collet 70 may be dimensioned and configured for receiving the head 18. As such, the collet 70 and the head 18 may be rotatable and pivotable in relation to each other, thereby allowing the pedicle screw 10 to be repositioned in a plurality of orientations relative to the collet 70. The combination of the collet 70 and pedicle screw 10 may be inserted into the coupling 50. The pin 30 (see FIG. 1E) may align the collet 70 and the coupling 50 for maintaining a fixed relationship between them. As assembled, the pedicle screw 10 may be rotatable and pivotable in relation to the collet 70 and the coupling 50 as will be discussed in further detail hereinbelow.

Furthermore, a set screw 90 (see FIG. 1E) may be provided to be receivable in the collet 70 such that the set screw 90 abuts the top surface of the head 18 of the pedicle screw 10, where the set screw 90 is releasably secured via a gripping tool (not shown). The pedicle screw 10 may be configured to have a slidable outer housing 50 over an inner housing 70 containing a spherically configured, pivotable screw head 18 and a removable spinal rod 92 (see FIG. 1F) wherein the outer housing 50 may be selectively positioned to fully lock the screw head 18 and the spinal rod 92 in position within the inner housing 70 via the set screw 90. Moreover, the outer housing 50 may be selectively positioned to lock only the screw head 18 in position while permitting a sliding and rotating motion of the spinal rod 92 about its long axis within the inner housing 70. The use of the set screw 90 may not be utilized until a full lock condition for the screw-rod construct is required which would eliminate the motion of the rod 92 in both a rotating and sliding means.

Figure 1E:
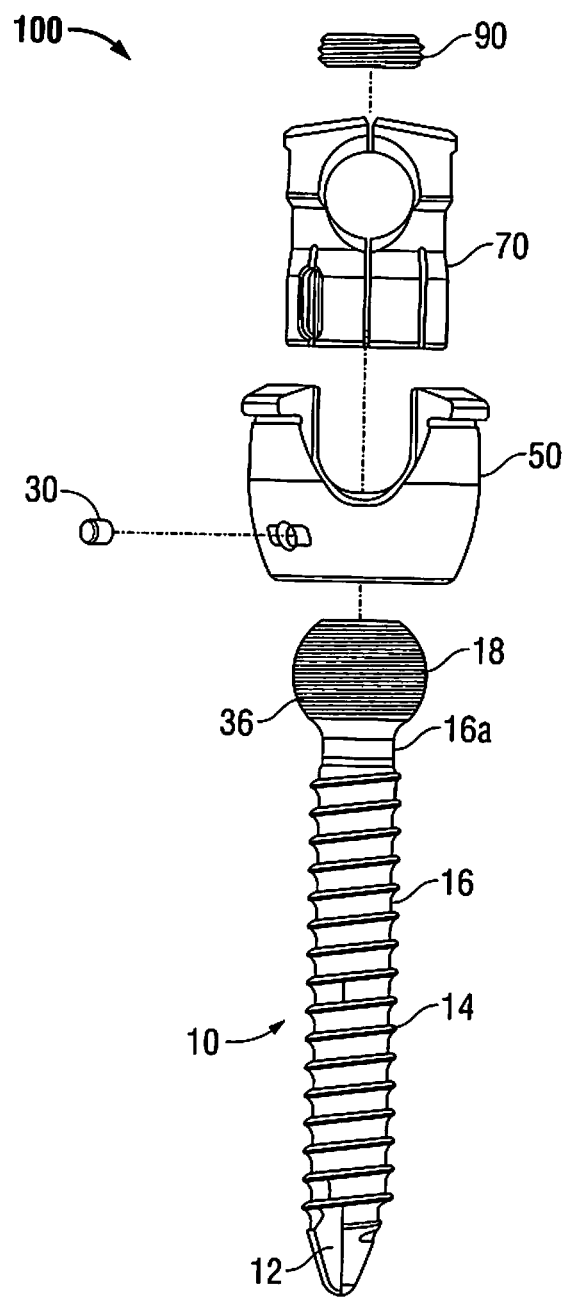
FIG. 1E is an exploded side view of the pedicle screw of FIG. 1A with parts separated illustrating a pedicle screw, a coupling, a collet, a pin, and an set screw, in accordance with the present disclosure.
Figure 1F:
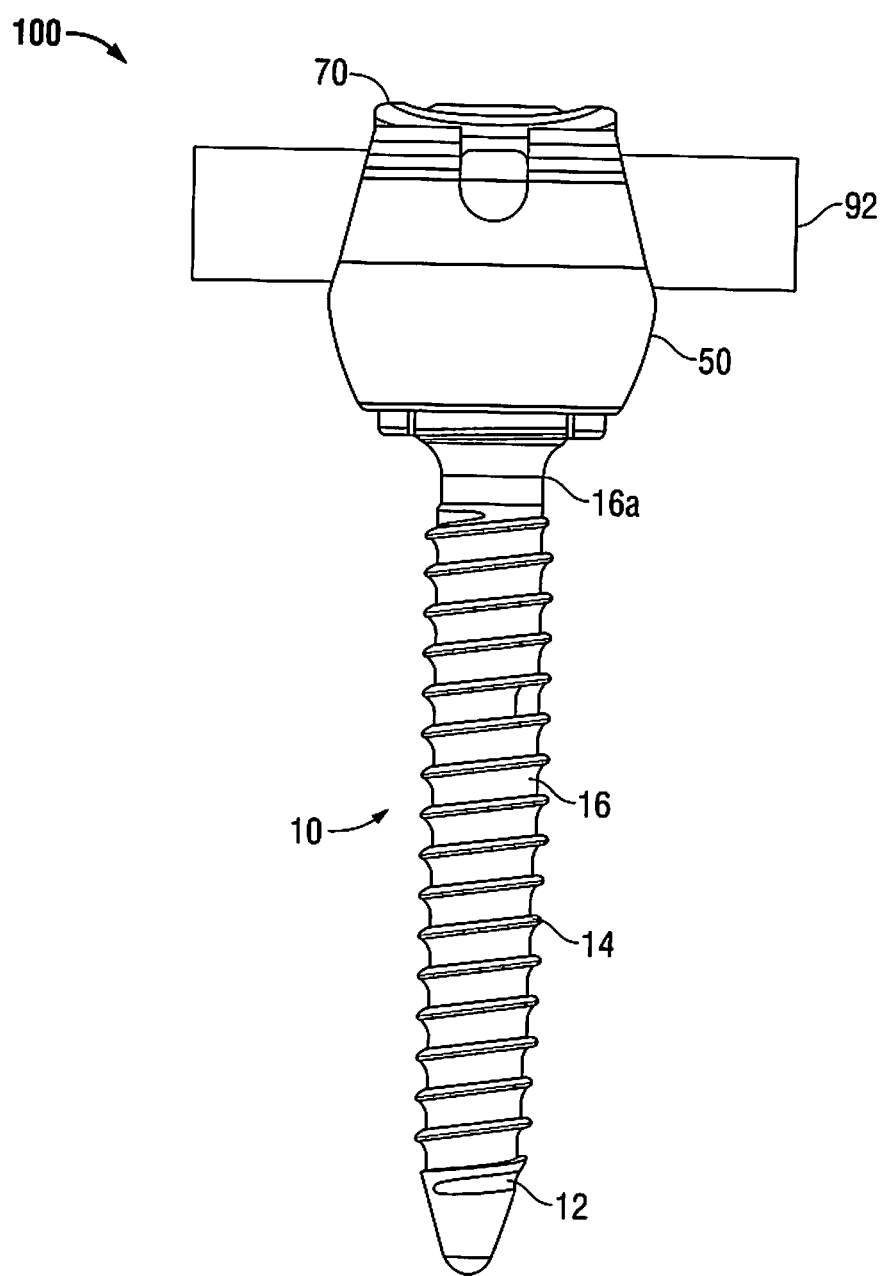
FIG. 1F is a side view of the pedicle screw of FIG. 1A having a rod passing therethrough, in accordance with the present disclosure.

The set screw 90 may be used for retaining the rod 92 (see FIG. 1F) in the screw head 18. The set screw 90 may be utilized with an internal or external thread on the inner housing 70 or outer housing 50, respectively. The set screw 90 may be utilized as a crimping feature over the top of the outer housing 50, thereby providing additional resistance to the potential separation of the rod 92 from the screw head assembly. Also, the inner housing 70 may be configured with internal screw threads (see FIG. 2D). Partial and full locking of the system 100 may be achieved when the outer housing 50 is translated in an upward manner by compressing the inner housing 70 around the rod member 92. The set screw 90, as shown in FIG. 1E, may be threaded into the inner housing 70 and may compress on the rod member 92 thereby providing additional holding force on the rod member 92.

Referring now to FIGS. 2A-2D, the collet 70 may have a generally cylindrical body portion 72 with an opening 74 extending axially therethrough. The body portion 72 may include a groove 77 that extends from the nadir of the saddle 78 towards the bottom of the body portion 72 and essentially bisects the body portion 72 along a central axis, and defines left and right sections of the body portion as viewed in FIGS.

2A, 2D. It is contemplated that a plurality of grooves 77 may be equally or unequally spaced apart around the circumference of the body portion 72.

The dimensions of the saddle 78 may vary according to the flexure of the wings 76. As the wings 76 are moved closer to each other, the saddle 78 decreases in size and when the wings 76 are moved away from each other, the saddle 78 increases in size. Allowing the saddle 78 to vary in size permits the collet 70 to accommodate rods 92 (see FIG. 1F) having differing outside diameters. Alternatively, compressing the wings 76 towards each other increasingly engages the outer surface of a rod 92 located in the saddle 78, thereby frictionally securing the rod 92 in a desired position.

Figure 2A:
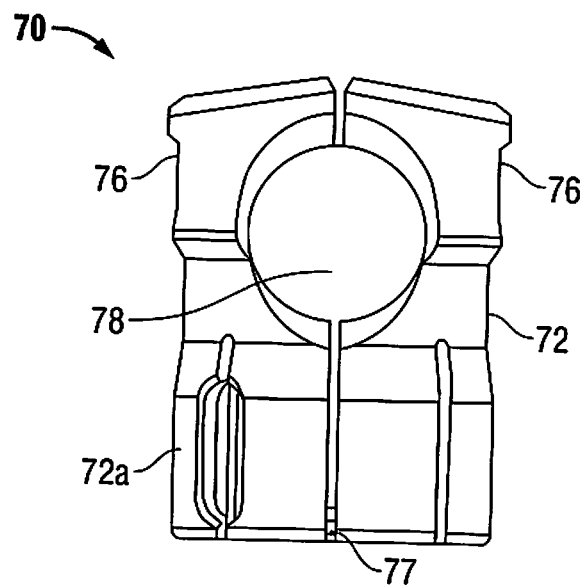
FIG. 2A is a front view of the collet, in accordance with the present disclosure.
Figure 2B:
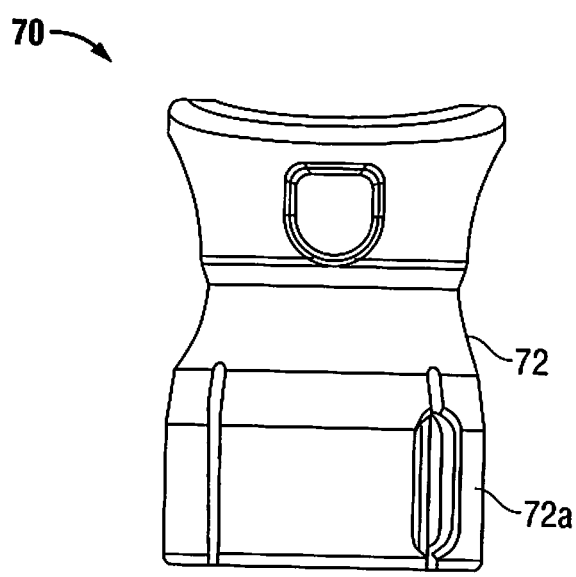
FIG. 2B is a side view of the collet of FIG. 2A, in accordance with the present disclosure.
Figure 2C:
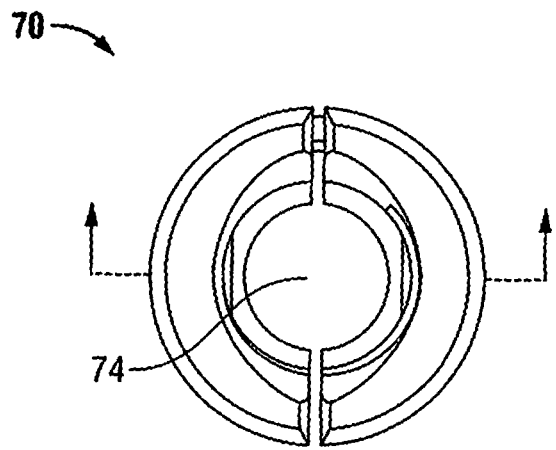
FIG. 2C is a top view of the collet of FIG. 2A, in accordance with the present disclosure.
Figure 2D:
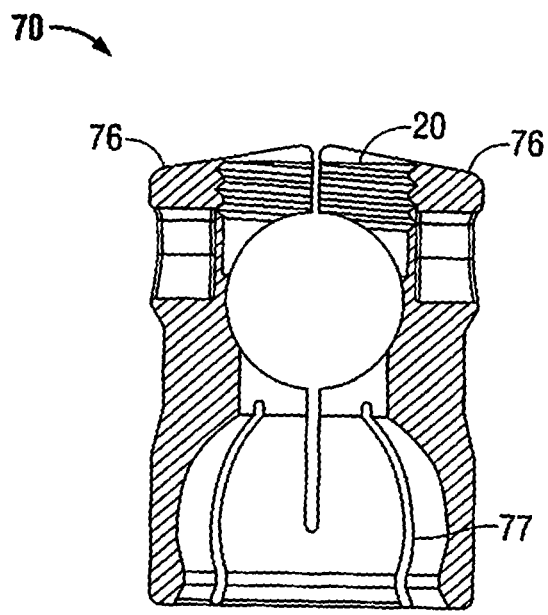
FIG. 2D is a front cross-sectional view of the collet of FIG. 2A taken along section line A-A of FIG. 2C, in accordance with the present disclosure.
Figure 3B:
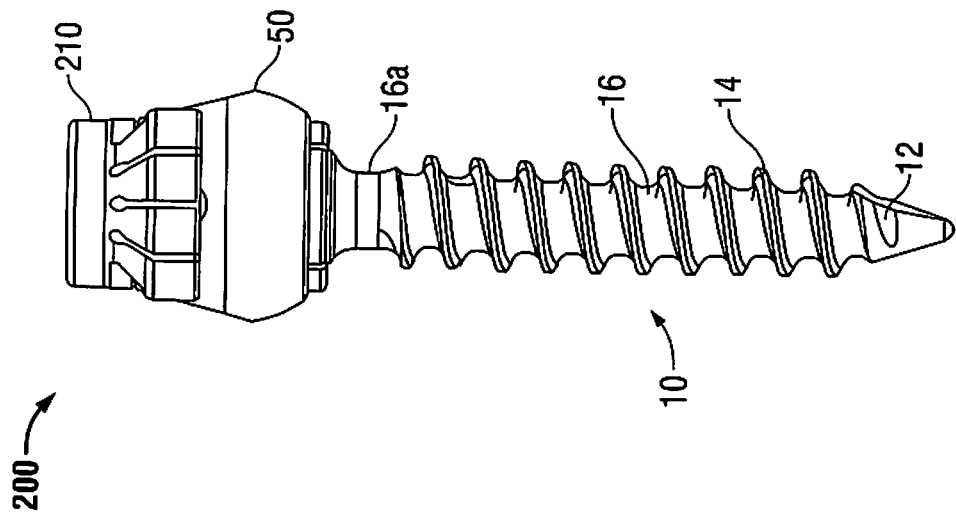
FIG. 3B is a side view of the pedicle screw of FIG. 3A, in accordance with an alternate embodiment of the present disclosure.
Figure 3A:
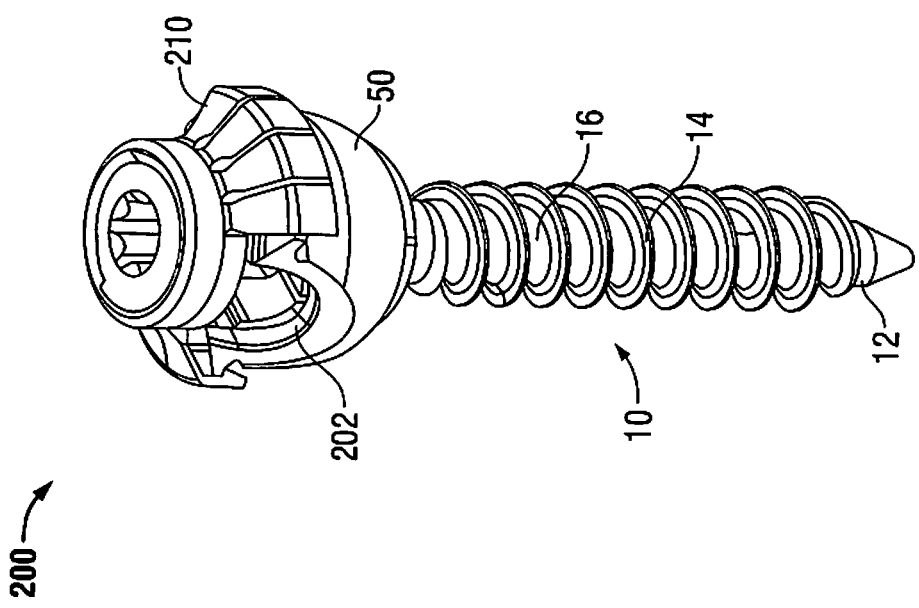
FIG. 3A is top perspective view of a pedicle screw having an outer housing top crimp clamp with set screw, in accordance with an alternate embodiment of the present disclosure.
Figure 3C:
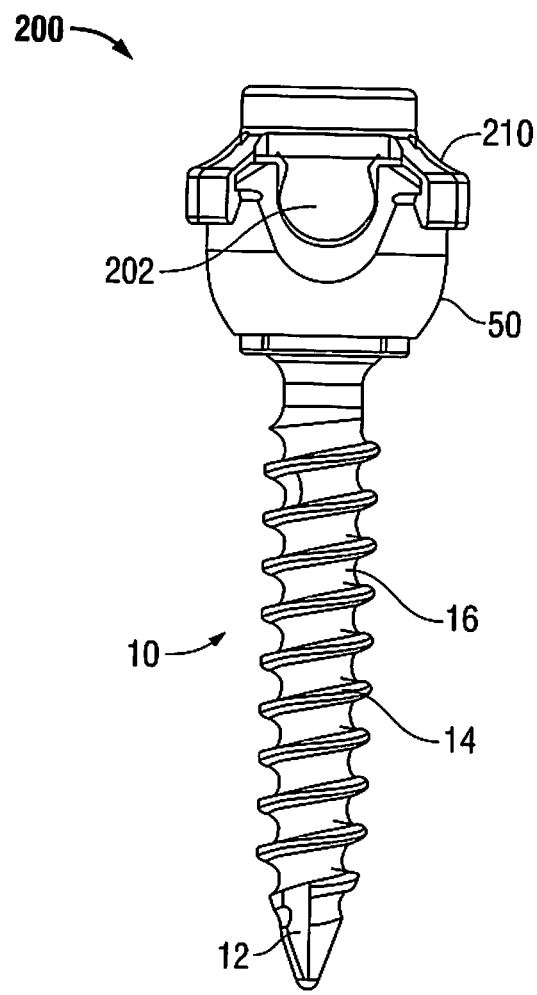
FIG. 3C is a front view of the pedicle screw of FIG. 3A, in accordance with an alternate embodiment of the present disclosure.
Figure 3D:
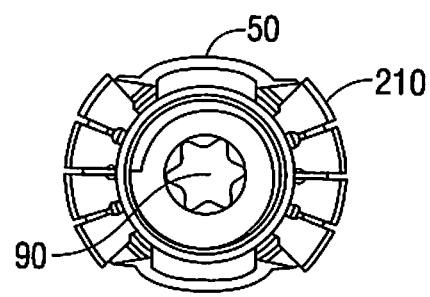
FIG. 3D is a top view of the pedicle screw of FIG. 3A, in accordance with an alternate embodiment of the present disclosure.
Figure 4B:
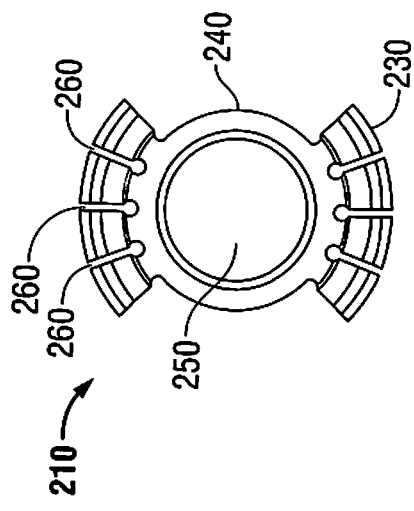
FIG. 4B is a top view of the housing top crimp clamp of FIG. 4A, in according with an alternate embodiment of the present disclosure.
Figure 4D:
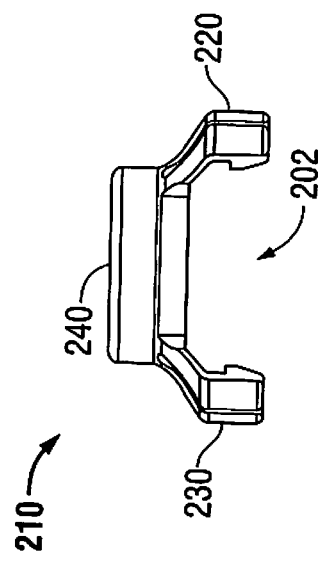
FIG. 4D is a front view of the housing top crimp clamp of FIG. 4A, in according with an alternate embodiment of the present disclosure.
Figure 4A:
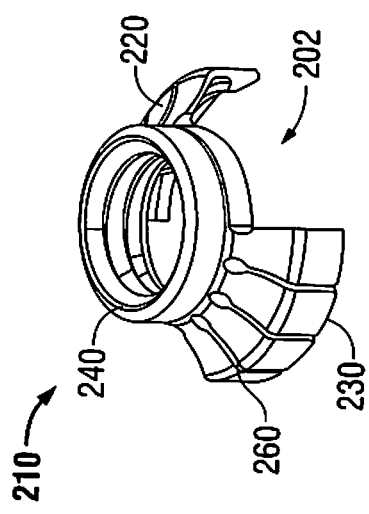
FIG. 4A is a top perspective view of a housing top crimp clamp, in according with an alternate embodiment of the present disclosure.
Figure 4C:
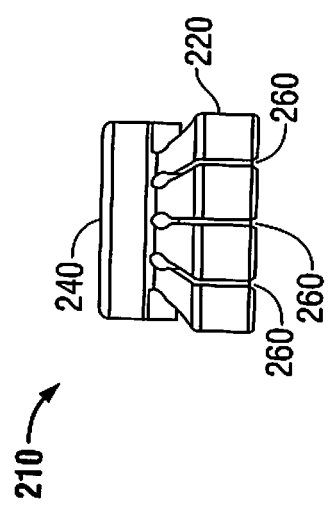
FIG. 4C is a side view of the housing top crimp clamp of FIG. 4A, in according with an alternate embodiment of the present disclosure.

In addition, the grooves 77 may extend to the bottom of the body portion 72 and may be open at the bottom of the body portion 72. It is contemplated that the grooves 77 may extend vertically into each of the wings 76. As configured, the grooves 77 may permit the front and rear sections of the body portion 72 to flex relative to the grooves 77. The body portion 72 may also include arcuate sections 72a to flex inwards and outwards from an initial position in response to compressive and tensile forces applied to the sections 72a. FIG. 2D illustrates how the set screw 90 is positioned within the collet 70. As shown, the set screw 90 is positioned within the wings 76 to define a region for receiving a rod 92 (see FIG. 1F). On the top surface of the head 18, a recess 20 is formed for receiving the set screw 90, as shown in FIG. 2D.

Referring back to FIGS. 1A-1F, the pedicle screw 10 includes a shank 16 having a helical thread 14 formed thereon. A cutting portion 12 is formed at a distal end of the pedicle screw 10. A head 18 is located at a proximal end of the pedicle screw 10. The head 18 includes a plurality of grooves 36 formed thereon and has an outer diameter that is greater than the outer diameter of the shank 16. On the top surface of the head 18, the top portion of the set screw 90 is shown (see FIG. 1D). The top portion of the set screw 90 is illustrated with a six-pointed star configuration for receiving the operative end of a suitable driving tool, but it is contemplated that other configurations may be used. A neck 16a extends between a bottom surface of the head 18 and the beginning of the helical thread 14. As configured, the neck 16a is unthreaded. As shown, at least a portion of the diameter of the neck 16a is less than the diameter of the bottom of the head 18 and the major diameter of the threaded portion of the shank 16.

Additional features of the assembled pedicle screw construct 100 will be discussed with reference to FIGS. 1A-1F. For example, the coupling 50 may include an inner annular lip (not shown) that is beveled. The lip may extend upwards and inwards from a bottom outer edge of the coupling 50. Additionally, the collet 70 may include an annular beveled lip (not shown) that also may extend upwards and inwards from bottom outer edge of the collet 70. An angle between the annular beveled lip of the coupling 50 and a centerline of the pedicle screw 10 may have a value between about 25 to about 75 degrees. By providing the coupling 50 and the collet 70 with beveled lips, there is a reduced interaction between the head 18 and the coupling 50 and/or the collet 70. In addition, the pedicle screw 10 has a neck 16a with a length and diameter that cooperate with the beveled lips for reducing interaction therebetween. That is, the length of the non-threaded neck portion 16a of the pedicle screw 10 may extend a distance from the bottom of the head 18 to a point beyond the beveled lip of the collet 70 and beveled lip of the coupling 50. Thus, the selected diameter of the neck 16a permits maximum angular motion of the pedicle screw 10 relative to the collet 70 and coupling 50. This creates a smooth transition zone between the unthreaded neck 16a and the collet 70 and the coupling 50. By reducing the interference between the neck 16a and the beveled lips in combination with the reduced interaction between the head 18 and the beveled lips, the pedicle screw 10 defines a cone of at least 70° with respect to a centerline of the pedicle screw construct. In another embodiment, the pedicle screw 10 has a conical range of motion that is at least 90°. In a further embodiment, the pedicle screw 10 has a conical range of motion that is at least 95°.

While the embodiments shown in FIGS. 1A-1F and 2A-2D suggest that the inner housing 70 is configured to be slid over the end of the rod 92 into position, it is contemplated that the top could be open to receive the rod 92 (see FIG. 1F), with the nut or screw threads disposed on the upwardly extending arms which define the opening to receive the rod 92. The rod 92 is slid through the saddle 78 of collet 70 to secure the rod 92 to the pedicle screw construct 100. When the inner housing 70 is moved into the outer housing 50 into a locked or partially locked position, the outer housing 50 surrounding the inner housing 70 may provide support for the upwardly extending arms of the inner housing 70. In this manner a set screw inserted to engage threads on the upwardly extending arms of the inner housing 70 is secure and provides additional locking of the rod 92 within the pedicle screw 10. Similarly, threads on the outside of the upwardly extending arms of the inner housing 70 may receive a nut, or inner and outer threads may receive a set screw nut combination to provide additional rod security.

An alternate embodiment of a pedicle screw construct 200 is shown in FIGS. 3A-3D. In this embodiment, pedicle screw construct 200 does not include the set screw 90 shown in FIGS. 1E and 2D. Instead, an outer housing top crimp clamp 210 is presented. The pedicle screw construct 200 is discussed in greater detail below.

Similar to the previous embodiment illustrated in FIGS. 1A-1F, the pedicle screw 200 of the present embodiment includes a pedicle screw 10 and a coupling 50. The pedicle screw 10 includes a shank 16 having a helical thread 14 formed thereon. A cutting portion 12 is formed at a distal end of the pedicle screw 10. A head 18 (not shown in this alternate embodiment) is located at a proximal end of the pedicle screw 10. A neck 16a (see FIGS. 3B, 3C) extends between a bottom surface of the head 18 and the beginning of the helical thread 14. Optionally, on the top surface of the head 18, a top surface of the set screw 90 may be shown (see FIG. 3D). The set screw 90 is illustrated with a six-pointed star configuration for receiving the operative end of a suitable driving tool, but it is contemplated that other configurations may be used.

As shown in FIGS. 3A-3D, a pedicle screw construct 200 includes a coupling 50, an outer housing top crimp clamp 210, and a pedicle screw 10. When assembled, the pedicle screw 10 may be rotatable and pivotable in relation to the clamp 210 and the coupling 50. Optionally, the coupling 50 may include a plurality of fingers (not shown) that are located in opposing regions of the coupling 50 and define a saddle 202 (see FIGS. 3A, 3C) having a generally U-shaped configuration. The U-shaped saddle 202 may be configured and dimensioned for receiving a rod 92 (see FIG. 1F).

The clamp 210 may include a pair of wings 220, 230 with an opening 250 (see FIG. 4B) extending axially therethrough. As illustrated in FIGS. 4A-4D, each wing 220, 230 may include one or more grooves 260 extending from the top portion towards the bottom portion of the clamp 210. Preferably, although not necessarily, grooves 260 would extend all the way through the wings 220, 230 of the clamp 210. This arrangement would allow the wings 220, 230 to flex away and towards each other allowing saddle 202 to accommodate rods 92 of various sizes.

Specifically, as seen in FIGS. 3A-3D, the top crimping clamp device 210 is fitted or positioned overtop a previously locked taper locked screw. The top crimp clamp 210, as shown in FIGS. 4A-4D may be capable of grasping the underside of the proximal flange of the outer housing 50. Then, by crimping, that is deforming the clamping flanges, the top crimp clamp 210 may be removably fixed or releasably secured to the outer housing 50 while providing a downward force on the rod member 92. Optionally, a set screw (not shown) may be threaded into the top crimp clamp 210, thus providing for supplemental fixation of the rod 92 in the screw. When secured, the set screw provides a downward force on the rod member 92 and an upward force where the clamping flanges are in gripping contact with the proximal flange of the outer housing 50.

The presently disclosed pedicle screw constructs 100, 200 may be adaptable for spinal procedures. In particular, the pedicle screw constructs 100, 200 may include a relatively short pedicle screw 10, which is suitable for procedures in the cervical region of the spine, since the forces and/or stresses applied to the pedicle screw 10 in the cervical region are lower than those of either the lumbar or the thoracic regions. It is contemplated that beveling the inner surfaces of the coupling and the collet/clamp in a pedicle screw construct 100, 200 for use in the thoracic or lumbar regions would increase their angular range of movement.

The presently disclosed pedicle screw constructs 100, 200 may be also be provided as a kit. The kit may include at least two of the multi-planar taper lock screw constructs 100, 200, at least one rod device 92, and surgical instruments having a configuration complementary to the configuration of the head of the pedicle screw 10 and configured to facilitate grasping of the screw head 18 for locking and/or unlocking of the rod 92. The kit may include any of the components discussed above with regard to pedicle screw constructs 100, 200.

While the foregoing description contemplates the use of a preferred design of taper lock screw, which provides advantages particularly when used in the areas of the spine such as the cervical spine where the amount of soft tissue covering the spine is less than in other regions of the spine, it is contemplated that a screw having increased angulation between the screw and the rod coupling housing may be achieved with other designs of screws.

In conclusion, to securely connect adjacent vertebrae not on a common plane, the example embodiments described above are presented to provide a multi-planar, taper lock screw that may be easily inserted and/or removed from the vertebral bone as desired. It is also desirable that such a screw be configured so that it may be locked into position in relation to the bone and the spinal rod without the need to exert any additional torque to the device or force on the patient. Additionally, in order to provide supplemental means for retaining the rod in the screw head, it is contemplated to utilize a set screw via internal or external thread on the inner or outer housing, respectively, or to utilize a crimping feature over the top of the outer housing, thereby providing additional resistance to the potential separation of the rod from the screw head assembly.

Moreover, the multi-planar taper lock screw having a proximal flange provides for a multi-planar screw for connection of a spinal rod to a first vertebra. The head of the screw may be easily and conveniently connected to a rod that may also be connected to an adjacent vertebra not in the same plane as the first vertebra. Also, the screw may be easily grasped by an operator using a complementary grasping tool to remove the rod when desired. The multi-planar taper lock screw is configured to be easily connected to the vertebra and then connected to a spinal rod without the additional application of torque.

It will be understood that various modifications may be made to the embodiments of the presently disclosed pedicle screw construct. Therefore, the above description should not be construed as limiting, but merely as exemplifications of embodiments. Those skilled in the art will envision other modifications within the scope and spirit of the present disclosure.

What is claimed is:

1. A surgical device comprising:
a coupling having an opening extending therethrough;
a collet configured to be receivable in the opening of the coupling, the coupling longitudinally repositionable with respect to the collet between a locked position and an unlocked position;
a pedicle screw having a head configured to be receivable in an opening of the collet, the pedicle screw comprising a shank, a head having a top and a bottom surface, and a neck between the bottom of the head and the shank, the head configured to be receivable in an opening of the collet such that the pedicle screw is movable throughout a plurality of positions when the coupling is in the unlocked position and the pedicle screw is in a fixed position when the coupling is in the locked position; and
a collet set screw in operable communication with a rod;
wherein the collet applies a first force to securely lock the rod in place without the aid of the collet set screw and the collet set screw is configured to apply a second force to the rod as supplemental support to the rod.

2. The surgical device of claim 1, wherein the pedicle screw has a conical range of motion of at least 70 degrees.

3. The surgical device of claim 1, wherein
the shank includes a helical thread formed thereon; and
the neck has a diameter that is less than a diameter of the bottom of the head or a diameter of the helical thread of the shank.

4. The surgical device of claim 1, wherein at least one groove extends from a bottom portion of the collet towards a bottom portion of a saddle of the collet.

5. The surgical device of claim 1, wherein the collet set screw is threaded within the collet.

6. The surgical device of claim 5, wherein the threaded collet set screw compresses the top surface of the head of the pedicle screw.

7. The surgical device of claim 1, wherein the rod is fixed in the collet when the coupling is in the locked position.

8. The surgical device of claim 1, wherein the second force is sufficient to maintain the rod and the collet set screw in place in the absence of the first force.

9. A surgical device comprising:
a coupling having an opening extending therethrough;
a clamp configured to be releasably secured to an outer portion of the coupling, the clamp having at least two wings for grasping the outer portion of the coupling and a centrally positioned opening; and
a pedicle screw having a head configured to be receivable in an opening of the coupling, the pedicle screw comprising a shank, a head having a top and a bottom surface, and a neck between the bottom of the head and the shank, the head configured to be receivable in an opening of the coupling such that the pedicle screw is movable throughout a plurality of positions;

wherein each of the wings includes a plurality of grooves, each of the plurality of grooves adapted and dimensioned to be linear and equally spaced apart from the other across a length of each of the wings.

10. The surgical device of claim 9, wherein the pedicle screw has a conical range of motion of at least 70 degrees.

11. The surgical device of claim 9, wherein
the shank includes a helical thread formed thereon; and
the neck has a diameter that is less than a diameter of the bottom of the head or a diameter of the helical thread of the shank.

12. The surgical device of claim 9, wherein the at least two wings of the clamp provide an additional force on the pedicle screw.

13. The surgical device of claim 9, wherein the centrally positioned opening of the clamp further includes an internal threaded configuration for receiving a set screw to provide an additional force on the pedicle screw.

14. A surgical device comprising:
a pedicle screw adapted to be in mechanical cooperation with a gripping tool;
a rod disposed in mechanical cooperation with the pedicle screw;
a first locking structure configured to secure the rod to the pedicle screw, the first locking structure includes a coupling in mechanical cooperation with a collet, the coupling longitudinally repositionable with respect to the collet between a first condition and a second condition, the pedicle screw repositionable with respect to the collet when the coupling is in the first condition; and
a second locking structure configured to secure the rod to the pedicle screw;
wherein the first locking structure applies a first force to securely lock the rod in place without the aid of the second locking structure and the second locking structure is configured to apply a second force to the rod as supplemental support to the rod.

15. The surgical device of claim 14, wherein the second locking structure includes a set screw in operable communication with the rod, the set screw configured to be receivable in the collet such that the set screw contacts a portion of the rod.

16. The surgical device of claim 14, wherein the second force is sufficient to maintain the rod and the second locking structure in place in the absence of the first force.

* * * * *